United States Patent [19]

Suzuki

[11] 4,105,687

[45] Aug. 8, 1978

[54] CYANOETHYLATION OF GLYCOLIC ESTERS

[75] Inventor: Shigeto Suzuki, San Francisco, Calif.

[73] Assignee: Chevron Research Company, San Francisco, Calif.

[21] Appl. No.: 763,279

[22] Filed: Jan. 27, 1977

[51] Int. Cl.$^2$ .................. C07C 120/00; C07C 121/16
[52] U.S. Cl. ................................ 260/465.4; 260/464; 260/465 D
[58] Field of Search ................ 260/465.4, 464, 465 D

[56] References Cited

U.S. PATENT DOCUMENTS

| | | | |
|---|---|---|---|
| 2,559,660 | 7/1951 | Rehberg | 260/465.4 |
| 3,017,434 | 1/1962 | Bulloff | 260/526 R |

OTHER PUBLICATIONS

Rehberg, et al., J.A.C.S., 74, (1952), 1095.
The Chemistry of Acrylonitrile, Cyanamid, 2nd ed., 1959, pp. 225-226.
Organic Reactions, vol. 5, (1949), p. 89.
Degering, "Organic Nitrogen Compounds", 1945, pp. 502-505.
Wagner and Zook, "Synthetic Organic Chemistry", 1953, pp. 590-609.

*Primary Examiner*—Joseph Paul Brust
*Attorney, Agent, or Firm*—D. A. Newell; John Stoner, Jr.; A. T. Bertolli

[57] ABSTRACT

Alkyl 2-cyanoethoxyacetate is prepared by cyanoethylation of alkyl glycolate in the presence of a metallic alkoxide under substantially anhydrous conditions. 2-Cyanoethoxyacetic acid is produced from this ester by saponification and acidification.

7 Claims, No Drawings

CYANOETHYLATION OF GLYCOLIC ESTERS

BACKGROUND OF THE INVENTION

This invention concerns alkyl esters of cyanoethoxyacetic acid and a process for preparing these compounds.

Acrylonitrile undergoes base-catalyzed addition reactions with practically any compound containing a reactive hydrogen, such as alcohols, mercaptans, hydrogen cyanide, acids, amines, phosphines and even ketones:

Sodium methoxide and sodium hydroxide have been used to catalyze the addition of alcohols to acrylonitrile. Because the product contains a cyanoethyl group, the process has been called cyanoethylation.

However, the esters of hydroxy acids have resisted cyanoethylation. For instance, *Organic Reactions*, Vol. V, pg. 89 (1949) reports that attempts to add ethyl glycolate to acrylonitrile have failed, "... only the esters of hydroxy acids have resisted cyanoethylation; attempts to add ethyl glycolate, ethyl lactate, and ethyl ricinoleate to acrylonitrile have failed".

SUMMARY OF THE INVENTION

It has now been found that alkyl glycolates can be added to acrylonitrile by carrying out the reaction in the presence of a metallic alkoxide under substantially anhydrous conditions. The alkyl group may have from 1 to 10 carbon atoms.

DETAILED DESCRIPTION OF THE INVENTION

This invention provides a process for preparing alkyl esters of 2-cyanoethoxyacetic acid. These compounds are useful chemical intermediates. For instance, they can be used to prepare dicarboxylic acids by hydrolysis of the ester and nitrile group. They can also be used to prepare amino esters by reduction of the nitrile group, or amino acids by reduction of the nitrile group and hydrolysis of the ester group. All of these compounds are useful as monomers for condensation polymerization to produce fiber-forming polymers. In addition, the ester group may be hydrolyzed to give 2-cyanoethoxyacetic acid, a new composition of matter, also useful as an intermediate in the synthesis of polymers.

2-Cyanoethoxyacetic acid and the esters thereof have the structure

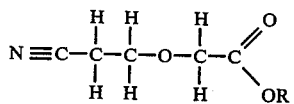

wherein R is hydrogen, an alkali metal cation or R', and R' is an alkyl group of 1 to 10 carbon atoms, a cycloalkyl group of 5 to 10 carbon atoms, aryl group of 6 to 12 carbon atoms, an aralkyl group of 7 to 10 carbon atoms, all of the above groups optionally containing halogen atoms, such as chlorine or bromine, hydroxy groups, alkoxy groups of 1 to 4 carbon atoms, or hydroxy alkoxy groups of 1 to 4 carbon atoms. Alkali metal cations include sodium, potassium, etc.

Representative alkyl groups include methyl, ethyl, n-propyl, i-propyl, n-pentyl, sec-butyl, t-butyl, n-octyl, n-decyl, 2-hydroxyethyl, 4-chlorobutyl, 2-methoxyethyl, 5-hydroxy-3-oxapentyl, etc. Representative cycloalkyl groups include cyclopentyl, cyclohexyl, cyclooctyl, 3-methylcyclohexyl, 4-hydroxycyclohexyl, 2-chlorocyclopentyl, 4-methoxycyclooctyl, etc. Representative aryl groups include phenyl, 4-methylphenyl, 3,5-dimethylphenyl, 3-ethylphenyl, 2-naphthyl, 2-methoxyphenyl, 2,4-dichlorophenyl, etc. Representative aralkyl groups include 2-phenylethyl, 3-phenoxypropyl, 2-(4-chlorophenyl)ethyl, 2-(4-methoxyphenyl)ethyl, etc.

The compounds are prepared by a process which comprises contacting esters of glycolic acid with acrylonitrile in the presence of a metallic alkoxide under substantially anhydrous conditions. As used herein, the term metallic alkoxide refers to organic compounds in which the hydrogen atom of a hydroxyl group of that compound is replaced by a metallic atom. Thus, the term includes both aliphatic and aromatic hydroxy containing compounds, commonly referred to as alcohols and phenols, respectively. Preferred alcohols are methanol and ethanol; the preferred hydroxy aromatic is phenol. The reaction proceeds rapidly to produce yields on the order of 70 mol percent and higher at temperatures of from about 0° C to about 120° C, preferably from about 20° C to about 100° C; and at normal pressure. Increased pressures can be used but are not necessary under most circumstances. Equimolar amounts of reactants can be used. Typically the acrylonitrile to glycolate mol ratio will vary from about 2:1 to 1:5. Of course, excess amounts of either reactant can be used. The reactants can be contacted using conventional batch or continuous methods. Under batch conditions, equilibrium is reached after a length of time which will depend upon the temperature of reaction, usually in the range of 2 to 6 hours at 50° C.

Substantially anhydrous conditions must be maintained during the reaction. The metallic alkoxide catalyst will react with water to form the corresponding hydroxide and a hydroxy containing organic compound. The hydroxide will not catalyze this reaction. Thus, in effect any water in the reaction zone acts as a contaminant. Accordingly, the term "substantially anhydrous" means that the molar amount of water, if any, which is present in the reaction zone must be substantially below the molar amount of alkoxide catalyst so that a relatively large concentration of alkoxide versus hydroxide is available to catalyze the reaction. In any event, the concentration of the hydroxide ion should be kept as low as possible.

The process is carried out in the presence of a catalytic amount of a metallic alkoxide such as sodium methoxide, or sodium phenoxide. These compounds are basic catalysts formed, for instance, by the reaction of an alcohol or a phenol with an active metal. Typical metallic alkoxides include the alkali metal alkoxides such as sodium, potassium, or lithium alkoxides; and alkaline earth metal alkoxides such as calcium or magnesium alkoxide. The molar amount of catalyst used in the process varies over a wide range. In general, from about 0.1% to about 10% is satisfactory; however, from about 0.5% to about 5% is preferred.

The following example illustrates practice of the process of this invention. The example, as those familiar with organic synthesis can appreciate, can be modified and is set forth for illustrative purposes.

EXAMPLE 1: PREPARATION OF METHYL 2-CYANOETHOXYACETATE

Acrylonitrile 79.5 g (1.5 mol) was added to a mixture of methyl glycolate 135 g (1.5 mol) and sodium methoxide 2.2 g (0.04 mol) with stirring at 42°–45° C during 78 min. The stirring was continued for 6.5 hours at 39–44° C. The progress of the reaction was followed by the use of GC analyses of the reaction mixture. An equilibrium was essentially reached after about 5 hours. The product mixture was diluted with chloroform and extracted with water. The original chloroform layer was subjected to vacuum distillation, and a total of 138.1 g (0.97 mol) methyl 2-cyanoethoxyacetate was collected (b.p. 95°–100° C/0.1 mm Hg). The structure of the cyanoester was confirmed by IR and NMR analyses. The distillation yield of the cyanoester was 64.5 mol percent, and the selectivity based on converted acrylonitrile was 75 mol percent.

Heating this methyl 2-cyanoethoxyacetate in an excess of aqueous sodium hydroxide will saponify the ester to produce the sodium salt of 2-cyanoethoxyacetic acid. Acidification by hydrochloric acid, followed by extraction with methylene chloride and subsequent evaporation of this solvent will give the free 2-cyanoethoxyacetic acid.

EXAMPLE 2: CYANOETHYLATION CATALYZED BY SODIUM PHENOXIDE

A 50 ml flask was charged with 0.47 g (0.005 mol) of phenol, 0.40 g (0.005 mol) of aqueous 50% sodium hydroxide, and 2 g of water. The resulting mixture was evaporated to dryness at 130° C under 2 mm pressure to give a solid sodium phenoxide.

After equipping the flask with a thermometer and reflux condenser, 9.0 g (0.10 mol) of methylglycolate was added. The ester was stirred, and after all of the sodium phenoxide had dissolved, 5.3 g (0.10 mol) of acrylonitrile was added all at once. After stirring at about 35° C for 45 minutes, the temperature was raised to about 105° C and held there for 60 minutes. At the end of this time, vapor phase chromatographic analysis showed that 83% of the acrylonitrile was converted, with a 56% selectivity to methyl 2-cyanoethoxyacetate.

WHAT IS CLAIMED IS:

1. A process for preparing a compound of the formula $$N\equiv C\text{-}CH_2\text{-}CH_2\text{-}O\text{-}CH_2COOR'$$

wherein R' is an alkyl group of 1 to 10 carbon atoms, a cycloalkyl group of 5 to 10 carbon atoms, an aryl group of 6 to 12 carbon atoms, an aralkyl group of 7 to 10 carbon atoms, or R" and R" is any of the groups defined by R' containing one or more substituents selected from halogen atoms, hydroxy groups, alkoxy groups of 1 to 4 carbon atoms, or hydroxy alkoxy groups of 1 to 4 carbon atoms, which comprises contacting a glycolate compound of the formula $$HO\text{-}CH_2\text{-}\underset{\underset{O}{\|}}{C}\text{-}OR'$$

wherein R' is as defined above, with acrylonitrile in the presence of a metallic alkoxide under anhydrous conditions.

2. A process according to claim 1 wherein said metallic alkoxide is sodium methoxide.

3. A process in accordance with claim 1 carried out at a temperature of from about 0° C to about 120° C.

4. A process in accordance with claim 1 carried out at a molar ratio of acrylonitrile to glycolic acid or ester of from about 2:1 to about 1:5.

5. A process in accordance with claim 1 carried out in the presence of from about 0.1 to 10.0 mol percent of a metallic alkoxide.

6. A process in accordance with claim 5 carried out in the presence of from about 0.5 to 5.0 mol percent of a metallic alkoxide.

7. A process in accordance with claim 1 wherein methyl glycolate is the glycolate compound and the product is 2-cyanoethoxymethylacetate.

* * * * *